United States Patent [19]

Socaris et al.

[11] Patent Number: 5,329,921
[45] Date of Patent: Jul. 19, 1994

[54] ENDOTRACHEAL TUBE

[76] Inventors: Spiro Socaris, 1 Alden Ct., Delmar, N.Y. 12054; Martha G. Kowalik, 35 Oakwood St., Albany, N.Y. 12208

[21] Appl. No.: 24,641

[22] Filed: Mar. 1, 1993

[51] Int. Cl.⁵ .................... A61M 16/04; A61M 25/00
[52] U.S. Cl. ...................... 128/207.14; 128/205.24; 128/203.12; 128/207.16; 604/86; 604/88; 604/244; 604/248; 138/103
[58] Field of Search ............... 138/103; 251/206, 208; 137/68.1; 604/244, 248, 86, 87, 88; 128/912, 200.24, 205.24, 203.12, 203.13, 207.14, 207.16, 202.13, 207.15, DIG. 26

[56] References Cited

U.S. PATENT DOCUMENTS

| | | | |
|---|---|---|---|
| 3,276,472 | 10/1966 | Jinkens | 604/248 X |
| 3,993,059 | 11/1976 | Sjöstrand | 128/205.13 |
| 4,219,021 | 8/1980 | Fink | 604/248 X |
| 4,351,328 | 9/1982 | Bodai | 128/202.16 |
| 4,506,665 | 3/1985 | Andrews et al. | 128/912 X |
| 4,552,142 | 11/1985 | Hoffman et al. | 128/207.16 |
| 4,646,733 | 3/1987 | Stroh et al. | 128/207.16 |
| 4,655,214 | 4/1987 | Linder | 128/207.18 |
| 4,738,265 | 4/1988 | Ritchart | 251/208 X |
| 4,790,832 | 12/1988 | Lopez | 604/283 |
| 4,821,714 | 4/1989 | Smelser | 128/207.14 |
| 4,840,173 | 6/1989 | Porter, III | 128/207.15 |
| 4,852,610 | 8/1989 | McHugh | 251/208 X |
| 4,955,375 | 9/1990 | Martinez | 128/207.14 |
| 4,967,743 | 11/1990 | Lambert | 128/202.16 |
| 4,967,759 | 11/1990 | Teves | 128/715 |
| 5,029,580 | 7/1991 | Radford et al. | 128/207.14 |
| 5,054,484 | 10/1991 | Hebecer, Jr. | 128/207.16 |
| 5,203,771 | 4/1993 | Melker et al. | 604/53 |

FOREIGN PATENT DOCUMENTS 2805354 9/1978 Fed. Rep. of Germany ...... 604/248
2122095 1/1984 United Kingdom ............... 128/912

OTHER PUBLICATIONS

"Hi-Lo Jet ™ Tracheal Tube" Advertisement, Date Unknown.

Primary Examiner—Edgar S. Burr
Assistant Examiner—Eric P. Raciti
Attorney, Agent, or Firm—Heslin & Rothenberg

[57] ABSTRACT

An improved endotracheal tube and an adapter for a standard endotracheal tube allow the performance of various medical procedures while maintaining continuity of respiration and protecting the care-provider from contact with potentially hazardous body fluids. The adapter comprises a rigid plastic Y-tube having a very large bore stopcock in one arm. In a preferred embodiment the endotracheal tube adapter further comprises a puncturable, resealing membrane having a first face in fluid communication with the interior of the adapter and a second face accessible to the exterior of the adapter. The adapter may additionally include an inflatable cuff circumferentially disposed within a bore of one of the tubes so as to allow axial engagement of a cylindrical object disposed within the bore of the tube. A single unit endotracheal tube assembly comprising the adapter and a conventional endotracheal tube is also disclosed.

18 Claims, 5 Drawing Sheets

ENDOTRACHEAL TUBE

BACKGROUND OF THE INVENTION

1. Field of the Invention

The invention relates to an improved endotracheal tube or an adapter for a standard endotracheal tube to allow the performance of various medical procedures while maintaining continuity of respiration.

2. Information Disclosure

Endotracheal intubation is the insertion of a hollow, pliable tube into the trachea. In human patients the tube is usually passed through the mouth, or less commonly through the nose, into the trachea extending approximately to the carina, anterior to a position between the second and fourth thoracic vertebrae. After the endotracheal tube is placed in the correct anatomical position, the end extending from the mouth (or nose) is attached to an oxygen source and mechanical ventilation is performed. The tube is commonly 14 to 30 cm long, 2.5 to 9.5 mm inside diameter and is furnished with a tapered adapter at the top for attaching the mechanical ventilator. A conventional endotracheal tube is shown in FIG. 1. Endotracheal intubation is indicated (1) when there is inadequate spontaneous ventilation or when there is evidence of insufficient oxygenation and the inadequacy is not corrected by supplemental oxygen from a mask or nasal cannula; (2) when there is a need to control and remove pulmonary secretions; (3) when drugs are to be administered directly into the lung and (4) when there is a need to provide airway protection in an obtunded patient or a patient with a depressed gag reflex. In an emergency setting, endotracheal intubation is often performed as a precaution when there is a possibility of any of the foregoing conditions.

The insertion and manipulation of a conventional endotracheal tube, particularly in an emergency, is fraught with potential hazard to the care provider because of the risk of contacting infected body fluids. In the past several years there has been world wide attention to the problem of contamination with regard to several problematic contagious diseases. Three major diseases posing a threat to patients and health care providers in the context of endotracheal intubation are: (1) AIDS (Acquired Immunodeficiency Syndrome), the pulmonary symptom presentation of which includes pneumonia, M-tuberculosis, and bronchiolitis; (2) drug resistant pulmonary tuberculosis; and (3) meningitis. All three can be spread by contact with pulmonary secretions of infected patients.

These and other respiratory infective diseases have contributed to the awareness that care providers must treat the blood and body fluids of all patients as potentially infectious and this awareness has given rise to the establishment of a set of "Universal Precautions."

Conventional endotracheal tubes pose a significant risk of contamination whenever the respiratory circuit is broken, and the circuit must be broken to administer drugs, to irrigate or to suction.

Among the more common conditions that require endotracheal intubation is cardiopulmonary arrest, which is treated commonly in hospital emergency departments and in pre-hospital settings. Typically, in patients experiencing cardiopulmonary arrest, mechanical ventilation with oxygen is in itself not sufficient to resuscitate successfully. Therefore, in addition to artificial ventilation, certain drugs may be necessary to help "restart" the heart. These drugs may be introduced into the patient's bloodstream via an intravenous cannula placed in a systemic vein, such as an arm vein or large chest vein (in contrast to a pulmonary vessel). However, in recent years, it has been found that certain life-saving drugs, such as epinephrine, atropine, and lidocaine, also may be administered through the pulmonary (lung) vasculature. Patients receiving these drugs for cardiopulmonary arrest, or receiving other drugs such as naloxone and valium for other indications, via the pulmonary route respond in a similar fashion to those patients receiving drugs via systemic (arm or chest) administration. As a result, it is now the accepted standard practice to use the endotracheal route for life-saving drug administration if for some reason systemic venous access is not available.

Since cannulating a systemic vein is time-consuming or even impossible in many situations, and since time is of the essence in administering life-saving drugs, the endotracheal route is often used in an emergency setting. Currently, the accepted technique for endotracheally administering drugs involves the injection of the selected drug into the proximal end of the tube and then "blowing" the drug down the tube into the lungs. Injection of the drug into the proximal end of the endotracheal tube using conventional tubes requires hyperventilating the patient, disconnecting the mechanical ventilator from the top of the endotracheal tube, instilling the medication and reattaching the ventilator. During the period of instillation, when the top of the tube is open, the medication, along with a certain amount of sputum, is often expelled back out as a result of cardiac compression efforts or as the result of an involuntary cough reflex due to irritation of the lungs. When there are thick pulmonary secretions, saline is also administered and the lungs are suctioned. This operation, as well, requires hyperventilating and breaking the circuit, once again exposing the care provider to risk of contact with infected fluids. The problem is exacerbated in this case because the significant accumulation of secretions and saline triggers a cough reflex which shoots the secretions out of the open tube. Since the intervention must be repeated every five to ten minutes in many cases, there is an enormous risk of exposure to infected fluids on the part of the care provider and a significant hazard to the patient as well because of the cycles of hyperventilation and absence of ventilation.

There is thus a need for an improved endotracheal tube that would allow uninterrupted mechanical ventilation and that would protect the care provider from exposure to contaminated fluids.

Another problem that occasionally arises during the instillation of drugs into the open end of the endotracheal tube is that of the needle dislodging from the syringe that is being used to administer drugs or saline into the tube. For administration many drugs and saline are drawn up into a medical syringe via an attached hypodermic needle. The needle is attached to the syringe by a tapered friction connector. When the plunger on the syringe is pushed to expel the fluid, pressure builds up in the area of the connector, and if there is no back pressure on the fitting from the shaft of the needle, the needle has been known to dislodge from the syringe and travel down the endotracheal tube, causing serious complications.

There is thus a further need for an improved means of allowing the introduction of medication into the endotracheal tube while preventing the introduction of other foreign matter and objects.

SUMMARY OF THE INVENTION

It is an object of invention to provide an endotracheal tube that allows uninterrupted mechanical ventilation while minimizing chances of exposing a care provider to contaminated fluids.

It is a further object to provide an endotracheal tube that allows the introduction of both medication and mechanical devices, such as suction tubes, into the lung of a patient during mechanical ventilation.

It is a further object to provide an endotracheal tube that can be used with standard, commercially available syringes, bronchoscopes and suction tubes.

These and other objects, features and advantages are provided by the present invention which comprises an endotracheal tube adapter for mounting on an end of an endotracheal tube external to a patient comprising:

(a) an elongated rigid plastic first tube having first and second ends, said first end being adapted to provide a substantially air-tight seal with said end of said endotracheal tube; said second end being adapted to provide a substantially air-tight seal with a device for ventilating a patient;

(b) a second tube having first and second ends, said first end of said second tube attached to said first tube between said first tube first and second ends so as to provide substantially air-tight communication between the bore of said first and said second tubes;

(c) a stopcock positioned in said second tube, said stopcock controllable between two positions, a closed position wherein fluid communication between segments of said second tube on opposite sides of said stopcock is prevented and an open position wherein fluid communication between segments of said second tube on opposite sides of said stopcock is substantially unimpeded, said stopcock having a bore which is between 50% and 110% of the bore of said second tube.

Preferably the endotracheal tube adapter further comprises a puncturable, resealing membrane having a first face in fluid communication with the interior of the adapter and a second face accessible to the exterior of the adapter.

The puncturable, resealing membrane can be positioned in a third tube. The third tube can extend from the first tube, or the third tube can extend from the second tube. Alternatively, the puncturable resealing membrane can be positioned in the stopcock such that when the stopcock is in a closed position, the membrane has a first face in fluid communication with the interior of the adapter and a second face accessible to the exterior of the adapter.

Preferably the stopcock has a bore of about 2.5 mm to about 9.5 mm.

The endotracheal tube adapter may additionally include an inflatable cuff circumferentially disposed within a bore of one of the tubes so as to allow axial engagement of a cylindrical object disposed within the bore of the tube. The cuff may be disposed within the second tube between the stopcock and the first tube, or between the stopcock and the second end. The cuff may also be self contained in its own adapter which may be fastened to the second end of the second tube via a friction connector as needed.

In another aspect, the invention relates to an endotracheal tube assembly comprising:

(a) a long, hollow, pliable tube having an inside diameter from about 2 mm and to about 10 mm and a length from about 10 cm to about 40 cm;

(b) An elongated first rigid tube having first and second ends, said first end being contiguous with said pliable tube, said second end being adapted to provide a substantially air-tight seal with a device for ventilating a patient;

(c) a second rigid tube having first and second ends, said first end of said second rigid tube attached to said first rigid tube between said first tube first and second ends so as to provide substantially air-tight communication between the bore of said first and said second rigid tubes;

(d) a stopcock positioned in said second rigid tube, said stopcock controllable between two positions, a closed position wherein fluid communication between segments of said second tube on opposite sides of said stopcock is prevented and an open position wherein fluid communication between segments of said second tube on opposite sides of said stopcock is substantially unimpeded, said stopcock having a bore which is between 50% and 110% of the bore of said second tube.

The endotracheal tube assembly of this aspect may incorporate all the features of the adapter aspect.

BRIEF DESCRIPTION OF THE DRAWINGS

FIG. 8 is a side view of an alternate geometry for an adapter of the invention.

DETAILED DESCRIPTION OF THE INVENTION

Figure 1:
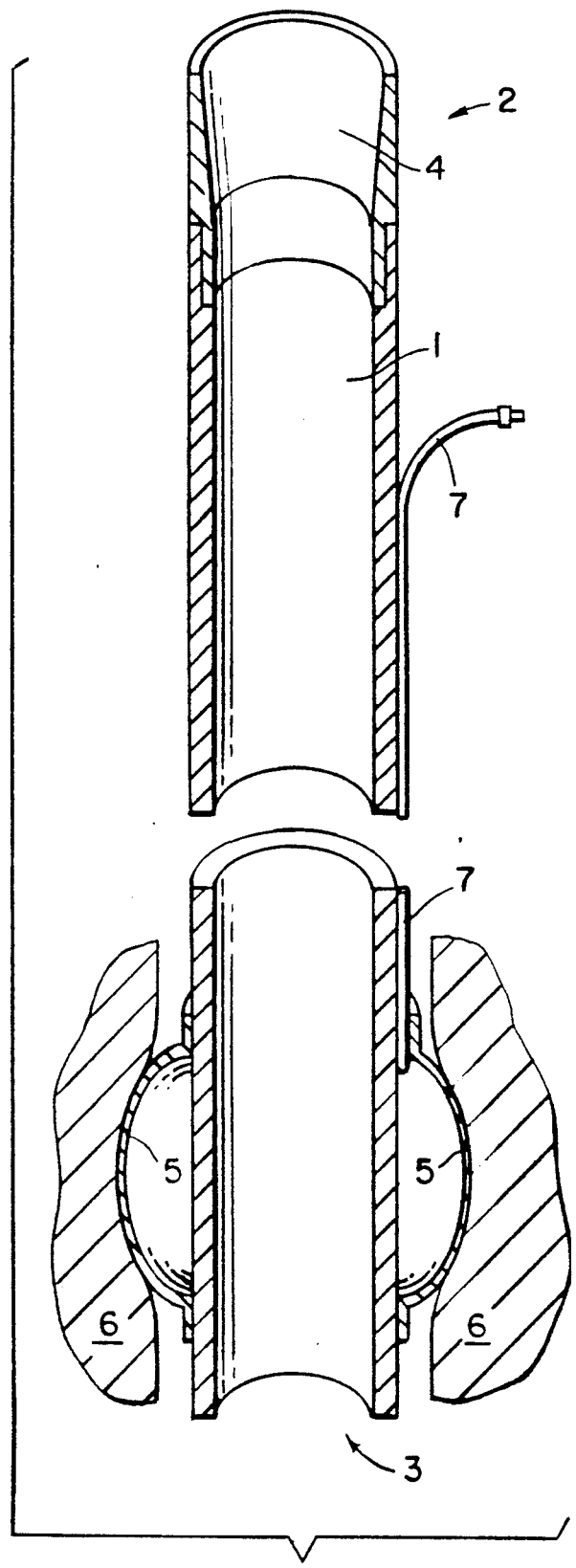
FIG. 1 is a side view, partially in cross-section, of an endotracheal tube of the art.

The improved endotracheal tube of the invention is more easily understood by reference to the drawings. FIG. 1 shows a conventional endotracheal tube of the type that is presently commercially available and in use in most hospitals and ambulances. The device comprises a long, pliable hollow tube 1 having an upper end 2, which in use is located outside a patient's mouth, and a lower end 3, which in use is usually located within a patient's trachea just above the bifurcation into the primary bronchi. The upper end 2 is commonly fitted with a female friction fitting 4 allowing the attachment of mechanical ventilating devices (not shown). In addition, there is often an inflatable cuff 5 which secures the lower end of the tube within the walls of the trachea 6. In use, the tube is inserted through the mouth (or less frequently, the nose). When the lower end is suitably positioned, the cuff 5 which was in a collapsed state, is inflated through a small, secondary tube 7.

As discussed above, the introduction of medication or of mechanical devices such as bronchoscopes and suction tubes into the trachea requires the disconnection of the means for ventilation that is attached to fitting 4 with the attendant opportunity for fluids to erupt from the open end.

Currently, prior to breaking the ventilatory circuit, for the administration of drugs or for suctioning, the patient should be hyperventilated. This is generally performed adequately in a hospital setting. In a pre-hospital setting, however, the stressful and frequently chaotic atmosphere during a resuscitation often result in hyperventilation being performed poorly or not at all, to the detriment of the patient. The device of the invention eliminates the need for performing hyperventilation, thereby eliminating one more function that needs to be accomplished during a resuscitation and increasing the chances of a successful resuscitation.

Figure 2:
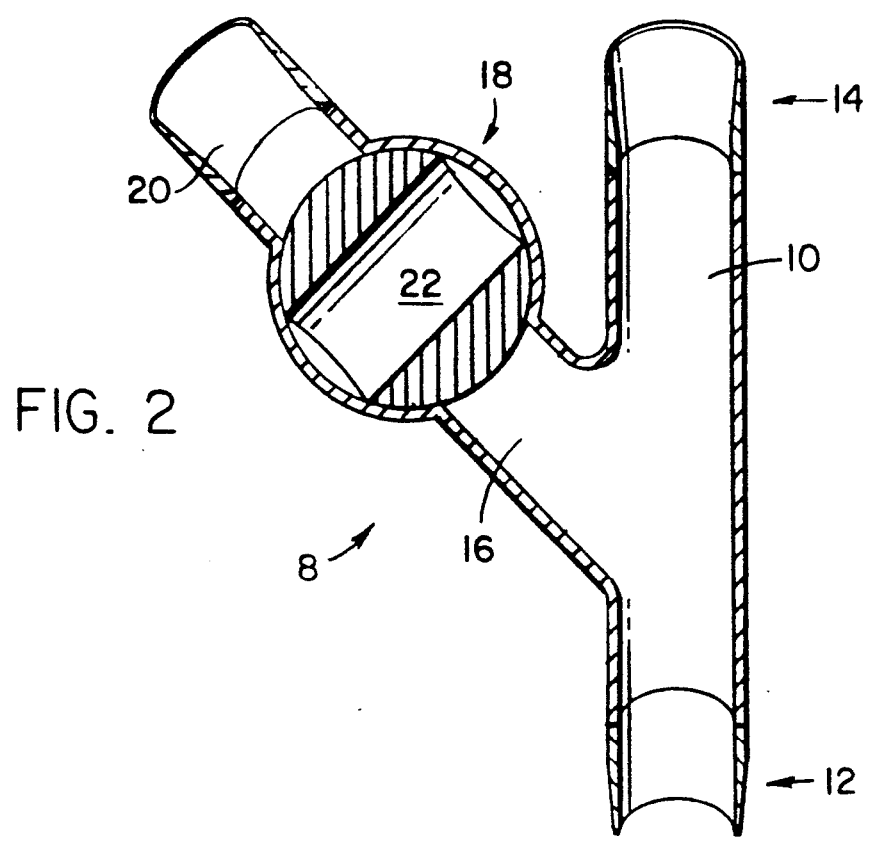
FIG. 2 is a side view, in cross-section, of one embodiment of an endotracheal tube adapter according to the invention.

FIG. 2 illustrates one embodiment of the present invention, an adapter 8 to be interposed between the endotracheal tube and the means for ventilation by attachment at female friction fitting 4. The improved adapter comprises an elongated rigid plastic first tube 10 having an end 12 which mates with the female friction fitting 4 of a standard endotracheal tube and second end 14 which mates (preferably via a second friction fitting) with the means for ventilation (not shown). A second rigid plastic tube 16 meets the first tube, preferably at a fairly acute angle so that bronchoscopes, suction tubes and the like can be readily inserted through tube 16 into tube 10 and out end 12. The second tube includes a stopcock 18 which in the illustration is shown in the closed position. The distal end of the second tube may optionally be fitted with a female friction fitting 20 as well. The bore 22 of the stopcock 18 is large enough to allow standard bronchoscopes or suction tubes to pass through without hanging up on the stopcock. Ideally the bore will be the same as the inside diameter of the tube 16, but stopcocks of smaller bore could be used as long as the device to be inserted would not hang up on the stopcock. Thus, for example, a 6 or 7 mm bore could be used in a 9 mm tube having a tapered shoulder leading to the stopcock. As a result, the bore 22 can be about 50 to 110% of the bore of the tube 16. The bore is preferably about 75-100% and most preferably 100% of the bore of the tube. It could also be slightly more than 100% of the tube bore, but there is no advantage to a stopcock bore much larger than the tube bore. This simplest embodiment of the invention can be further improved as shown in FIGS. 3, 4 and 5.

Figure 3:
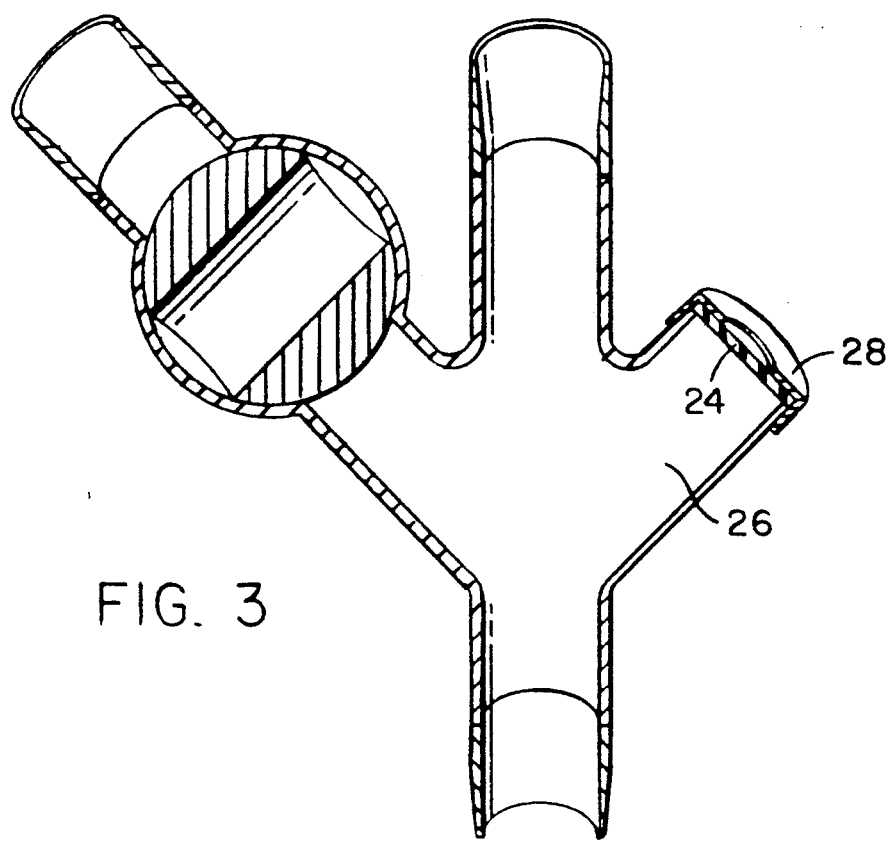
FIG. 3 is a side view, in cross-section, of a second embodiment of an endotracheal tube adapter according to the invention.

FIG. 3 illustrates a second embodiment including a puncturable, resealing membrane 24 which in this case is contained in a third arm 27 of the adapter. The membrane 24 can be made of any of the common rubber or silicone polymers well known for the purpose of allowing a hypodermic needle to penetrate into the interior and resealing when the needle is removed. The membrane can be attached to the arm 27 by a crimped aluminum band 29 or other means well known in the injection art. The membrane could also be contained on the surface of the second arm or in an arm attached thereto. The placement is not critical as long as a hypodermic needle inserted through the membrane has access to the interior of the endotracheal tube.

Figure 4:
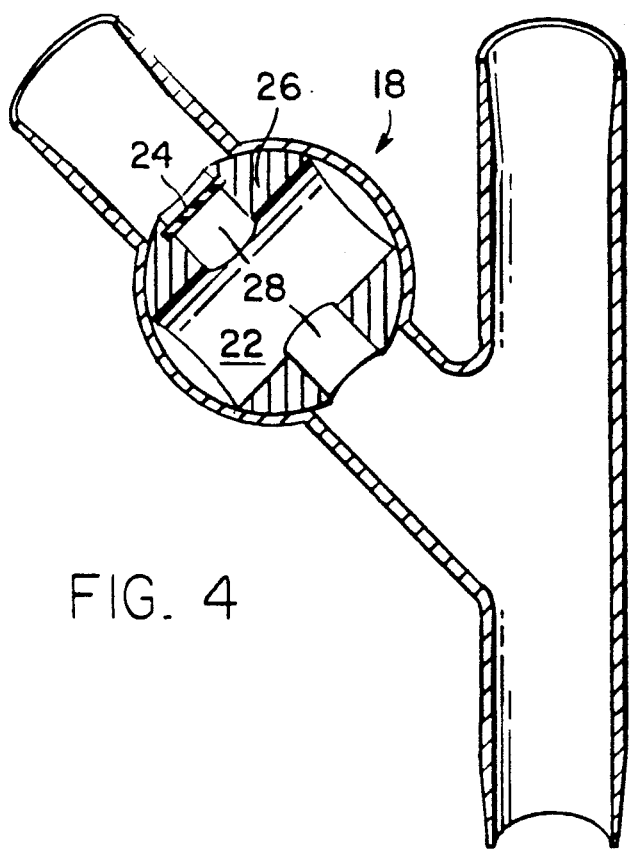
FIG. 4 is a side view, in cross-section, of a third embodiment of an endotracheal tube adapter according to the invention.
Figure 5:
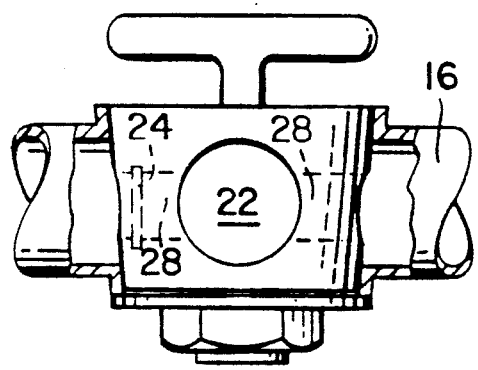
FIG. 5 is a perspective view of a stopcock rotating element.

A third embodiment is illustrated in FIGS. 4 and 5. In this case the puncturable membrane 24 is located on a face of the rotating element 26 of the stopcock 18. The puncturable membrane is in communication with a passage 28 through the rotating element 26 so that a hypodermic needle inserted through the membrane can deliver medication into the interior of the endotracheal tube adapter when the stopcock is in the closed position i.e., the large bore 22 of the rotating element 26 is not aligned with the bore of the tube. The puncturable membrane must be flush with or recessed below the surface of the rotating element so that the stopcock can freely rotate to the open position. The membrane can be held within the passage 28 by friction, by a shoulder and retaining ring or by adhesive.

Figure 6:
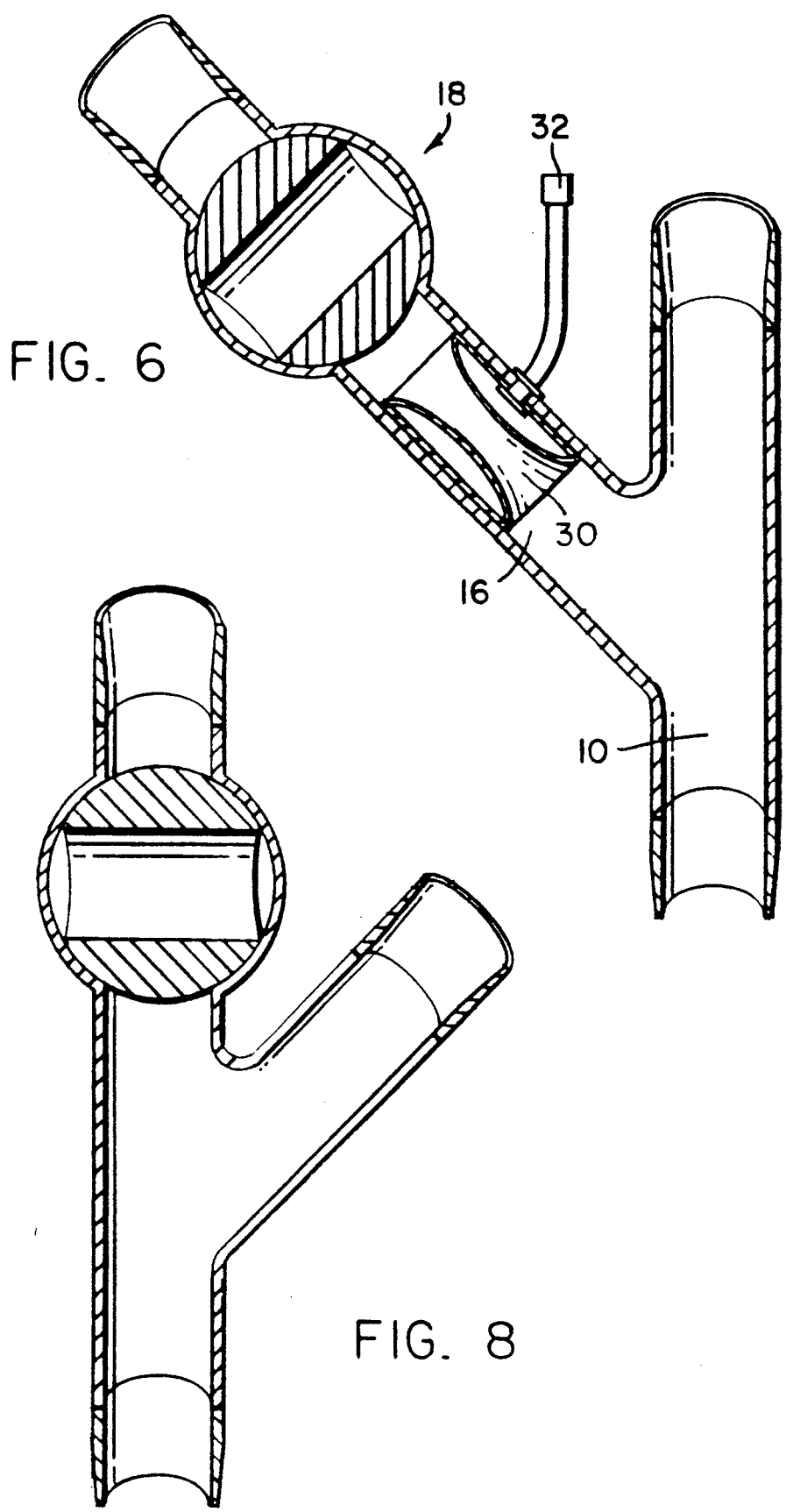
FIG. 6 is a side view in cross-section of an embodiment of the invention having an internal inflatable cuff.

A further improvement is provided by the inclusion of an inflatable cuff 30 as shown in FIG. 6. Inflatable cuffs are well known in the art and their operation is described for example in U.S. Pat. No. 4,967,759. In this case, the cuff is secured to the inside of one of the tubes so that whatever device may be inserted through stopcock 18 can be axially engaged and held in position. The cuff may be located as shown, within tube 16, or as not shown, within tube 10 below the intersection of the two tubes, within tube 16 but exterior to the stopcock 18, i.e., in the region of the open end, or self contained in its own adapter which may be fastened to the end of tube at 20. Different locations have different advantages. Devices with cuffs above the stopcock are easier to fabricate, but more susceptible to inadvertent needle punctures. The cuff is inflated and deflated by attaching a syringe at fitting 32.

Figure 7:
FIG. 7 is a side view of a single-unit endotracheal tube according to the invention.

The foregoing description has characterized various embodiments of improved endotracheal adapters. It will be obvious that the adapter may be structurally integrated into the endotracheal tube as well. Such a device is illustrated in FIG. 7. In this case the lower end 12 of the adapter shown in FIG. 2 is structurally integrated into the upper end 2 of the endotracheal tube shown in FIG. 1 to produce the single unit shown in FIG. 7. All of the modifications and improvements described above for the adapter may be incorporated as well into the single unit improved endotracheal tube.

The representations shown in FIG. 2 through 7 depict a configuration wherein the first rigid tube is straight and the second rigid tube (containing the stopcock) inserts into the first. There is no reason, in principle, that the second rigid tube (containing the stopcock) could not be straight and the first tube be angled. This alternate arrangement, illustrated in FIG. 8, may be advantageous in some situations and falls within the scope of the invention.

While the invention has been particularly shown and described with reference to preferred embodiments thereof, it will be understood by those skilled in the art that other changes in form and details may be made therein without departing from the spirit and scope of the invention.

We claim:

1. An endotracheal tube adapter for mounting on an end of an endotracheal tube external to a patient comprising:
    (a) an elongated rigid plastic first tube having first and second ends, said first end being adapted to provide a substantially air-tight seal when fitted with an endotracheal tube; said second end being adapted to provide a substantially air-tight seal when fitted with a device for ventilating a patient;
    (b) a second tube having first and second ends, said first end of said second tube attached to said first tube between said first tube and second ends so as to provide substantially air-tight communication between the bore of said first and said second tubes thereby forming a common interior;

(c) a stopcock positioned in said second tube so as to divide said second tube into two segments, said stopcock controllable between two positions, a closed position wherein fluid communication between said segments of said second tube is prevented and an open position wherein fluid communication between said segments of said second tube is substantially unimpeded, said stopcock having a bore which is between 50% and 110% of the bore of said second tube.

2. An endotracheal tube adapter according to claim 1 further comprising a puncturable resealing membrane having a first and a second face, said membrane being positioned in said stopcock such that when said stopcock is in a closed position, said puncturable, resealing membrane has a first face in fluid communication with the common interior of said adapter and a second face accessible from the exterior of said adapter.

3. An endotracheal tube adapter according to claim 1 wherein both of said stopcock and said second tube have a bore of 2.5 mm to 9.5 mm.

4. An endotracheal tube adapter according to claim 1 further comprising a puncturable, resealing membrane having a first face in fluid communication with the common interior of said adapter and a second face accessible from the exterior of said adapter.

5. An endotracheal tube adapter according to claim 4 wherein said puncturable, resealing membrane is positioned in a third tube, said third tube extending from said first tube and having a bore in fluid communication with said first tube.

6. An endotracheal tube adapter according to claim 4 wherein said puncturable, resealing membrane is positioned in a third tube, said third tube extending from said first tube and having a bore in fluid communication with said first tube.

7. An endotracheal tube adapter according to claim 1 additionally comprising an inflatable cuff circumferentially disposed within a bore of one of said tubes so as to allow radial engagement between said cuff and a cylindrical object disposed within said bore of said tube.

8. An endotracheal tube adapter according to claim 7 wherein said cuff is disposed within said second tube between aid stopcock and said first tube.

9. An endotracheal tube adapter according to claim 7 wherein said cuff is disposed within said second tube between aid stopcock and said second end.

10. An endotracheal tube assembly comprising:
(a) a long, hollow, pliable tube having an inside diameter from about 2 mm to about 10 mm and a length from about 10 cm to about 40 cm;
(b) An elongated first rigid tube having first and second ends, said first end being contiguous with said pliable tube, said second end being adapted to provide a substantially air-tight seal when fitted with a device for ventilating a patient;
(c) a second rigid tube having first and second ends, said first end of said second rigid tube attached to said first rigid tube between said first rigid tube first and second ends so as to provide substantially airtight communication between the base of said first and said second rigid tubes thereby forming a common interior;
(d) a stopcock positioned in said second rigid tube, so as to divide said second tube into two segments said stopcock controllable between two positions, a closed position wherein fluid communication between said segments of said second tube is prevented and an open position wherein fluid communication between said segments of said second tube is substantially unimpeded, said stopcock having a bore which is between 50% and 110% of the bore of said second tube.

11. An endotracheal tube assembly according to claim 10 further comprising a puncturable resealing membrane, said membrane being positioned in said stopcock such that when said stopcock is in a closed position, said puncturable, resealing membrane has a first face in fluid communication with the common interior of said adapter and a second face accessible from the exterior of said adapter.

12. An endotracheal tube assembly according to claim 10 wherein both of said stopcock and said second tube have a bore of 2.5 mm to 9.5 mm.

13. An endotracheal tube assembly according to claim 10 further comprising a puncturable, resealing membrane having a first face in fluid communication with the common interior of said adapter and a second face accessible from the exterior of said adapter.

14. An endotracheal tube assembly according to claim 13 wherein said puncturable, resealing membrane is positioned in a third tube, said third tube extending from said first tube and having a bore in fluid communication with said first tube.

15. An endotracheal tube assembly according to claim 13 wherein said puncturable, resealing membrane is positioned in a third tube, said third tube extending from said second tube and having a bore in fluid communication with said first tube.

16. An endotracheal tube assembly according to claim 10 additionally comprising an inflatable cuff circumferentially disposed within a bore of one of said tubes so as to allow radial engagement between said cuff and a cylindrical object disposed within said bore of said tube.

17. An endotracheal tube assembly according to claim 16 wherein said cuff is disposed within said second tube between said stopcock and said first tube.

18. An endotracheal tube assembly according to claim 16 wherein said cuff is disposed within said second tube between said stopcock and said second end.

* * * * *

UNITED STATES PATENT AND TRADEMARK OFFICE
CERTIFICATE OF CORRECTION

PATENT NO. : 5,329,921
DATED : Jul. 19, 1994
INVENTOR(S) : Socaris et al.

It is certified that error appears in the above-indentified patent and that said Letters Patent is hereby corrected as shown below:

<u>In the claims</u>:

Column 7, line 38, delete "first" and substitute therefor —second—.

Column 7, line 48, delete "aid" and substitute therefor —said—.

Column 7, line 51, delete "aid" and substitute therefor —said—.

Signed and Sealed this

Eighth Day of November, 1994

Attest:

BRUCE LEHMAN

Attesting Officer     *Commissioner of Patents and Trademarks*